US012690770B2

(12) United States Patent

Edelman et al.

(10) Patent No.: US 12,690,770 B2

(45) Date of Patent: Jul. 28, 2026

(54) SYSTEM AND METHOD FOR T1 RELAXATION ENHANCED STEADY-STATE MRI

(71) Applicant: Endeavor Health Clinical Operations, Evanston, IL (US)

(72) Inventors: Robert R. Edelman, Highland Park, IL (US); Ioannis Koktzoglou, Arlington Heights, IL (US)

(73) Assignee: Endeavor Health Clinical Operations, Evanston, IL (US)

( * ) Notice: Subject to any disclaimer, the term of this patent is extended or adjusted under 35 U.S.C. 154(b) by 0 days.

(21) Appl. No.: 17/911,809

(22) PCT Filed: Mar. 11, 2021

(86) PCT No.: PCT/US2021/021895

§ 371 (c)(1),
(2) Date: Sep. 15, 2022

(87) PCT Pub. No.: WO2021/188355

PCT Pub. Date: Sep. 23, 2021

(65) Prior Publication Data

US 2023/0139038 A1 May 4, 2023

Related U.S. Application Data

(60) Provisional application No. 62/991,181, filed on Mar. 18, 2020.

(51) Int. Cl.
*A61B 5/00* (2006.01)
*A61B 5/055* (2006.01)
(Continued)

(52) U.S. Cl.
CPC ............ *A61B 5/0044* (2013.01); *A61B 5/055* (2013.01); *A61B 5/742* (2013.01); *G01R 33/385* (2013.01);
(Continued)

(58) Field of Classification Search
CPC ....... A61B 5/0044; A61B 5/055; A61B 5/742; A61B 2576/023; A61B 5/743;
(Continued)

(56) References Cited

U.S. PATENT DOCUMENTS 7,253,620 B1 8/2007 Derbyshire et al.
7,292,039 B1 11/2007 Laub et al.
(Continued)

FOREIGN PATENT DOCUMENTS

WO WO2019083936 5/2019

OTHER PUBLICATIONS

Johst, Sören, et al. "Time-of-flight magnetic resonance angiography at 7 T using venous saturation pulses with reduced flip angles." Investigative radiology 47.8 (2012): 445-450. (Year: 2012).*
(Continued)

*Primary Examiner* — Rishi R Patel

(74) *Attorney, Agent, or Firm* — Quarles & Brady LLP

(57) ABSTRACT

A method for generating magnetic resonance (MR) images of a subject includes performing, using a magnetic resonance imaging (MRI) system, a steady-state pulse sequence to acquire MR data from a region of interest in the subject. The steady-state pulse sequence includes a contrast-modifying (CM) radio frequency (RF) pulse applied periodically at a predetermined time interval followed by a gradient spoiler pulse. The CM RF pulse has a flip angle with a value determined based on a minimum Ernst angle for a set of one or more background tissues in the region of interest that the CM RF pulse is configured to suppress with respect to a
(Continued)

tissue of interest. The method further includes generating an image with Ti contrast based on the acquired MR data.

20 Claims, 3 Drawing Sheets

(51) Int. Cl.
| | |
|---|---|
| *G01R 33/385* | (2006.01) |
| *G01R 33/50* | (2006.01) |
| *G01R 33/561* | (2006.01) |

(52) U.S. Cl.
CPC ......... *G01R 33/50* (2013.01); *G01R 33/5614* (2013.01); *A61B 2576/023* (2013.01)

(58) Field of Classification Search
CPC .. G01R 33/385; G01R 33/50; G01R 33/5614; G01R 33/5635; G01R 33/448; G01R 33/543; G01R 33/4828; G01R 33/5607; G01R 33/5602

See application file for complete search history.

(56) References Cited

U.S. PATENT DOCUMENTS

| | | | | |
|---|---|---|---|---|
| 11,857,306 | B1 * | 1/2024 | Posse | .................. A61B 5/0042 |
| 2003/0176782 | A1 | 9/2003 | Graessner | |
| 2008/0081986 | A1 * | 4/2008 | Slavin | .................... A61B 5/055 |
| | | | | 600/410 |
| 2014/0050379 | A1 | 2/2014 | Miyazaki | |
| 2014/0084918 | A1 | 3/2014 | Kurokawa | |
| 2015/0185301 | A1 | 7/2015 | Hsu et al. | |
| 2017/0176562 | A1 | 6/2017 | Li et al. | |
| 2019/0025396 | A1 | 1/2019 | Edelman et al. | |

OTHER PUBLICATIONS

Schmalbrok P, Hacker VA, Rao A. Three-dimensional steady-state MR angiography of the lower extremities. J Magn Reson Imaging 1994; 4(2):223-30.

Kellman P. et al. Cardiac First-Pass Perfusion MRI Using 3D trueFISP Parallel Imaging USing TSENSE. Proc. Intl. Soc. Mag. Reson. Med. 11 (2004).

Chung Y. et al. Inversion Recovery Prepared PSIF for FLAIR at 7T. Proc. Intl. Soc. Mag. Reson. Med. 21 (2013).

Scheffler K, Heid O, Hennig J. Magnetization preparation during the steady state: fat-saturated 3D TrueFISP. Magn. Reson. Med. 2001; 45(6):1075-1080.

Derbyshire J.A. et al. S5FP: Spectrally Selective Suppression with Steady-State Free Precession. Magn. Reson. Med. 54:918-928 (2005).

Koktzoglou I. et al. Radial Fast Interrupted Steady-State (FISS) Magnetic Resonance Imaging. Magn. Reson. Med. 79:2077-2087 (2018).

Reeder SB, Herzka DA, McVeigh ER. Signal-to-noise ratio behavior of steady-state free precession. Magn Reson Med. 2004; 52: 123-130.

Miller KL, Tijssen RHN, Stikov N, Okell TW. Steady-state MRI: methods for neuroimaging. Imaging Med. 2011; 3(1), 93-105.

Edelman RR, Sheehan JJ, Dunkle E, Schindler N, Carr J, Koktzoglou I. Quiescent-interval single-shot unenhanced magnetic resonance angiography of peripheral vascular disease: Technical consideration and clinical feasibility. Magn Reson Med Apr. 2010; 63(4): 951-58.

Derbyshire J.A. et al. Reduction of Flow Artifacts in Balanced SSFP Imaging Using S5FP. Proc. Intl. Soc. Mag. Reson. Med. 16 (2008).

Koktzoglou I. et al. Radial Fast Interrupted Steady-State (FISS) Cine Imaging for the Evaluation of Heart Valves and Coronary Arteries. CMR 2018—A joint Euro(MR) SCMR Meeting Abstract Supplement. p. 196-197.

Edelman R.R. et al. Quantitative Coronary Flow Imaging Using Breath-hold Cine FISS Arterial Spin-Labeled MR Angiography. CMR—2018 A joint Euro(MR) SCMR Meeting Abstract Supplement. p. 391.

Edelman R.R. et al. Dynamic Flow Imaging and Quantification Using Cine FISS Arterial Spin Labeling. Proc. Intl. Soc. Mag. Reson. Med. 26(2018).

Edelman R.R. et al. Cardiovascular Cine Imaging and Flow Evaluation Using Fast Interrupted Steady-State (FISS) Magnetic Resonance. Journal of Cardiovascular Magnetic Resonance (2018) 20:12.

Marckmann P. et al. Nephrogenic Systemic Fibrosis Suspected Causative Role of Gadodiamide used for Contrast-Enhanced Magnetic Resonance Imaging, J. Am. Soc. Nephrol. 2006, 17(9) 2359-2362.

PCT/US2021/021895—International Search Report and Written Opinion—May 26, 2021, 11 pages.

Edelman, R., et al. "Twofold improved tumor-to-brain contrast using a novel T1 relaxation-enhanced steady-state (T1RESS) MRI technique." Science Advances 6.44 (Oct. 2020): eabd1635.

Extended European Search Report, corresponding to EP 21771095. 3, dated Mar. 12, 2024.

* cited by examiner

SYSTEM AND METHOD FOR T1 RELAXATION ENHANCED STEADY-STATE MRI

CROSS-REFERENCE TO RELATED APPLICATIONS

This application is a 371 application of PCT/US2021/021895 filed on Mar. 11, 2021, which claims priority to, and incorporates herein by reference in its entirety U.S. Ser. No. 62/991,181 filed Mar. 18, 2020, and entitled "System and Method for T1 Relaxation Enhanced Steady-State MRI." 2020, both of which are incorporated by reference herein in their entirety for all purposes.

STATEMENT REGARDING FEDERALLY SPONSORED RESEARCH

This invention was made with government support under R01HL130093 awarded by the National Institutes of Health. The government as certain rights in the invention.

BACKGROUND

The present disclosure relates to magnetic resonance imaging (MRI) and systems. More particularly, the present disclosure relates to systems and method for magnetic resonance imaging (MRI).

When a substance such as human tissue is subjected to a uniform magnetic field (polarizing field $B_0$), the individual magnetic moments of the nuclei in the tissue attempt to align with this polarizing field, but precess about it in random order at their characteristic Larmor frequency. If the substance, or tissue, is subjected to a magnetic field (excitation field $B_1$) that is in the x-y plane and that is near the Larmor frequency, the net aligned moment, $M_z$, may be rotated, or "tipped", into the x-y plane to produce a net transverse magnetic moment $M_{xy}$. A signal is emitted by the excited nuclei or "spins", after the excitation signal $B_1$ is terminated, and this signal may be received and processed to form an image.

When utilizing these "MR" signals to produce images, magnetic field gradients ($G_x$, $G_y$, and $G_z$) are employed. Typically, the region to be imaged is scanned by a sequence of measurement cycles in which these gradients vary according to the particular localization method being used. The resulting set of received MR signals are digitized and processed to reconstruct the image using one of many well-known reconstruction techniques.

The measurement cycle used to acquire each MR signal is performed under the direction of a pulse sequence produced by a pulse sequencer. Clinically available MRI systems store a library of such pulse sequences that can be prescribed to meet the needs of many different clinical applications. Research MRI systems include a library of clinically proven pulse sequences and they also enable the development of new pulse sequences.

Magnetic resonance angiography (MRA) uses the magnetic resonance phenomenon to produce images of the human vasculature. To enhance the diagnostic capability of MRA, a contrast agent such as gadolinium can be injected into the patient prior to the MRA scan. The goal of this contrast enhanced (CE) MRA method is to acquire the central k-space views at the moment the bolus of contrast agent is flowing through the vasculature of interest in order to benefit from improved contrast. That is, collection of the central lines of k-space during peak arterial enhancement, therefore, is key to the success of a CE-MRA exam. If the central lines of k-space are acquired prior to the arrival of contrast, severe image artifacts can limit the diagnostic information in the image. Alternatively, arterial images acquired after the passage of the peak arterial contrast are sometimes obscured by the enhancement of veins.

Recently, a rare and serious pathology involving fibrosis of skin, joints, eyes, and internal organs referred to as nephrogenic systemic fibrosis ("NSF") has been correlated to the administration of gadolinium-based contrast agents to patients undergoing contrast-enhanced MRA studies. The link between gadolinium-based contrast agents and NSF is described, for example, by P. Marckmann, et al., in "Nephrogenic Systemic Fibrosis: Suspected Causative Role of Gadodiamide Used for Contrast-Enhanced Magnetic Resonance Imaging," *J. Am. Soc. Nephrol.,* 2006; 17 (9):2359-2362. As a result of the increased incidence of NSF, methods for MRA that do not rely on the administration of a contrast agent to the patient have become an important field of research. However, current methods for non-contrast angiography are limited in their utility.

Steady-state gradient-echo acquisition techniques such as balanced steady-state free precession (bSSFP) are widely used in MRI because they provide a highly efficient acquisition with excellent signal-to-noise ratio. Steady-state MRI techniques permit the use of very short repetition times (TR), which makes them extremely efficient. Tissue contrast in steady-state acquisitions is dependent on the ratio $T_2/T_1$ of the tissue relaxation times. Certain tissues, specifically fluid, blood and fat, typically appear bright in the steady-state images. The bSSFP pulse sequence is commonly used in cardiovascular imaging and may be used to produce high signal from flowing blood, as well as from fluid-containing structures and fat. It is routinely used for cine and delayed enhanced imaging of the heart, for electrocardiogram (ECG)-gated NCMRA (non-contrast MR angiography) techniques such as quiescent interval slice-selective (QISS) and flow sensitive dephasing, as well as for niche applications such as constructive interference steady-state (CISS) for imaging of the inner ear structure. Balanced steady-state free precession techniques also have the property of being intrinsically compensated with respect to flow-induced phase shifts, so that flowing blood appears bright. Consequently, these techniques are routinely used to image the flow of blood in the heart (e.g., "cineangiography") and are used as the readout for non-contrast MR angiography techniques such as quiescent interval slice-selective MRA.

In order to maximize the conspicuity of flowing blood using steady-state sequences, it is necessary to suppress the signal intensity of other tissues, especially fat and fluid. Fat can be suppressed using chemical shift selective radiofrequency (RF) pulses or by periodically interrupting the echo train using pulses sequences such as fast interrupted steady-state (FISS). Other examples of variations of the bSSFP pulse sequences in which the echo train is intermittently paused and restarted to improve fat suppression are described in Scheffler K, Heid O, Hennig J. Magnetization preparation during the steady state: fat saturated 3D True-FISP. Magn Reson Med 2001; 45(6):1075-1080 and Derbyshire J A, Herzka D A, McVeigh E R. S5FP: spectrally selective suppression with steady state free precession. Magn Reson Med 2005; 54(4):918-928; U.S. Pat. No. 7,253, 620, Aug. 7, 2007. However, suppression of signal from fluid is problematic. One can suppress fluid signal using a fluid attenuation inversion recovery (FLAIR) technique, but this requires the use of a very long inversion time (e.g., >2 sec) that greatly reduces scan efficiency and prolongs scan time. Fluid signal may also be attenuated using a diffusion weighted preparation module, but this greatly increases the motion sensitivity of the pulse sequence and suppresses intravascular signal. It would therefore be desirable to provide a method for MRA that provides modified tissue contrast and fluid signal suppression and that can be used for contrast-enhanced and non-contrast angiography.

Although the tissue $T_1$ relaxation time of an enhancing tissue is reduced by the administration of contrast agent, so is the tissue $T_2$ relaxation time with the result that the ratio $T_2/T_1$, which determines tissue signal with steady-state MRI, is unchanged. In order to obtain $T_1$ weighting for imaging tissue enhancement following the administration of an extracellular paramagnetic contrast agent, bSSFP traditionally incorporates a preparatory 90° saturation recovery (e.g., for first-pass contrast-enhanced perfusion imaging) or 180° inversion recovery (IR) RF pulse (e.g., for imaging of delayed myocardial enhancement). These preparatory RF pulses are followed by a waiting period of at least a few hundred milliseconds prior to data collection. The use of a large flip angle preparatory RF pulse has the drawback of reducing the SNR and causing flow saturation artifacts with NCMRA. Moreover, the lengthy waiting period greatly diminishes scan efficiency compared with an unmodified bSSFP sequence. Consequently, steady-state pulse sequences are not typically useful for contrast-enhanced MRA, where a short scan time is needed in order to image the passage of contrast agent through the blood vessels of interest. As a result, contrast-enhanced MRI is almost always performed using fast low angle shot (FLASH) pulse sequences, even though the SNR is much lower than with a steady-state pulse sequence.

Contrast-enhanced MRI scans are typically acquired using a short repetition time $T_1$-weighted spoiled gradient-echo acquisition that applies a low flip angle excitation, where the low flip angle excitation only yields a fraction of the signal-to-noise ratio that could be obtained using a short repetition steady-state acquisition with a larger flip angle excitation. It would therefore also be desirable to provide a method for contrast-enhanced steady-state MRI where additional $T_1$ weighting is introduced without substantially reducing scan efficiency.

SUMMARY

In accordance with an embodiment, a method for generating magnetic resonance (MR) images of a subject includes performing, using a magnetic resonance imaging (MRI) system, a steady-state pulse sequence to acquire MR data from a region of interest in the subject. The steady-state pulse sequence includes a contrast-modifying (CM) radio frequency (RF) pulse applied periodically at a predetermined time interval followed by a gradient spoiler pulse. The CM RF pulse has a flip angle with a value determined based on a minimum Ernst angle for a set of one or more background tissues in the region of interest that the CM RF pulse is configured to suppress with respect to a tissue of interest. The method further includes generating an image with $T_1$ contrast based on the acquired MR data.

In accordance with another embodiment, a magnetic resonance imaging (MRI) system includes a magnet system configured to generate a polarizing magnetic field about at least a portion of a subject, a plurality of gradient coils configured to apply at least one gradient field to the polarizing magnetic field, a radio frequency (RF) system configured to apply an excitation field to the subject and to receive MR data from the subject and a computer system. The computer system is programmed to perform, using the MRI system, a steady-state pulse sequence to acquire MR data from a region of interest in the subject, the steady-state pulse sequence comprising a contrast-modifying (CM) radio frequency (RF) pulse applied periodically at a predetermined time interval followed by a gradient spoiler pulse. The CM RF pulse has a flip angle with a value determined based on a minimum Ernst angle for a set of one or more background tissues in the region of interest that the CM RF pulse is configured to suppress with respect to a tissue of interest. The computer system is further programmed to generate an image with $T_1$ contrast based on the acquired MR data.

The foregoing and other aspects and advantages of the invention will appear from the following description. In the description, reference is made to the accompanying drawings, which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION

Figure 1:
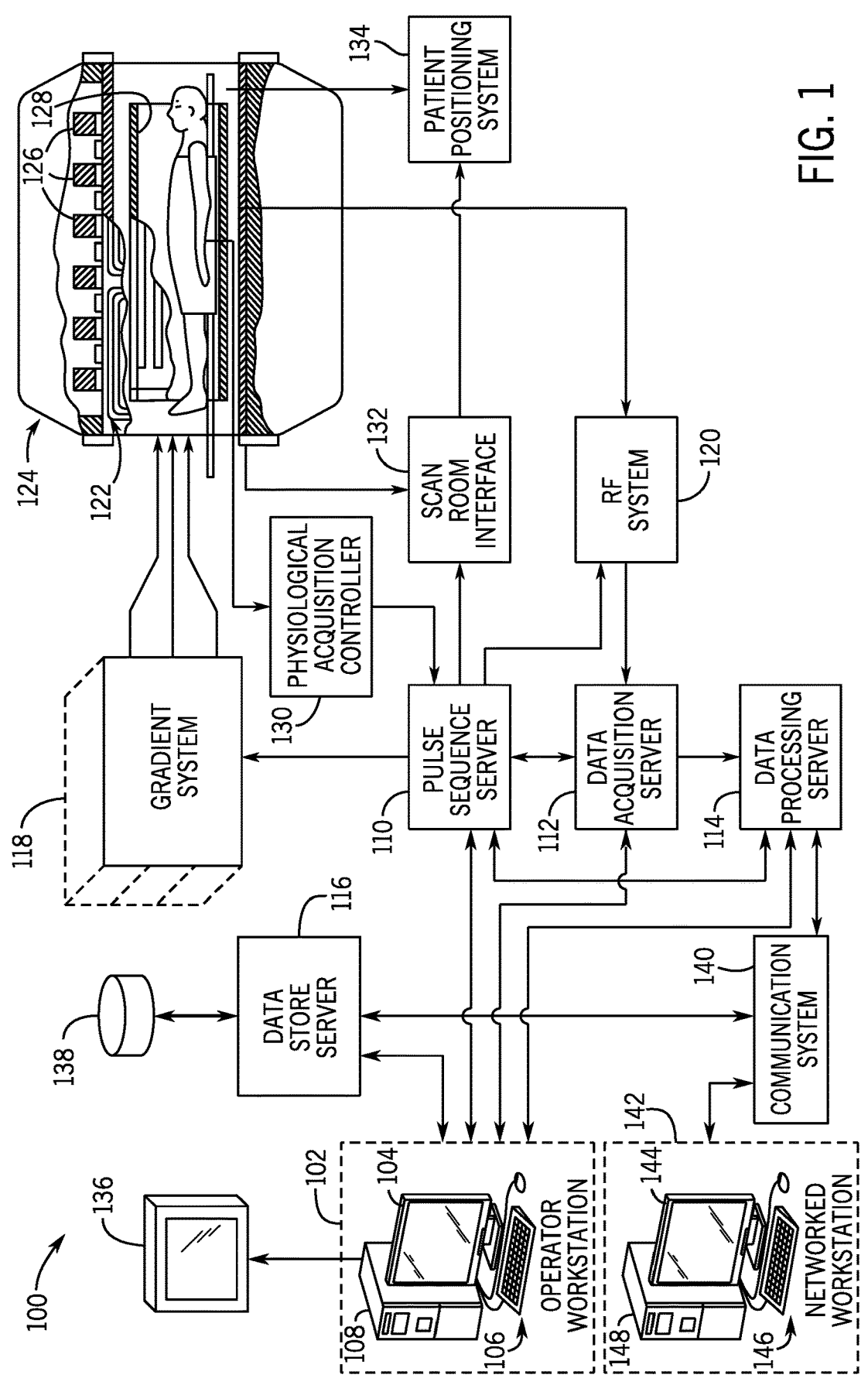
FIG. 1 is a block diagram of an example magnetic resonance imaging (MRI) system in accordance with an embodiment.

Referring now to FIG. 1, the disclosed systems and methods may be implemented using or designed to accompany a magnetic resonance imaging ("MRI") system 100, such as is illustrated in FIG. 1. The MRI system 100 includes an operator workstation 102, which will typically include a display 104, one or more input devices 106 (such as a keyboard and mouse or the like), and a processor 108. The processor 108 may include a commercially available programmable machine running a commercially available operating system. The operator workstation 102 provides the operator interface that enables scan prescriptions to be entered into the MRI system 100. In general, the operator workstation 102 may be coupled to multiple servers, including a pulse sequence server 110; a data acquisition server 112; a data processing server 114; and a data store server 116. The operator workstation 102 and each server 110, 112, 114, and 116 are connected to communicate with each other. For example, the servers 110, 112, 114, and 116 may be connected via a communication system 140, which may include any suitable network connection, whether wired, wireless, or a combination of both. As an example, the communication system 140 may include both proprietary or dedicated networks, as well as open networks, such as the internet.

The pulse sequence server 110 functions in response to instructions downloaded from the operator workstation 102 to operate a gradient system 118 and a radiofrequency ("RF") system 120. Gradient waveforms to perform the prescribed scan are produced and applied to the gradient system 118, which excites gradient coils in an assembly 122 to produce the magnetic field gradients $G_x$, $G_y$, $G_z$ used for position encoding magnetic resonance signals. The gradient coil assembly 122 forms part of a magnet assembly 124 that includes a polarizing magnet 126 and a whole-body RF coil 128.

RF waveforms are applied by the RF system 120 to the RF coil 128, or a separate local coil (not shown in FIG. 1), in order to perform the prescribed magnetic resonance pulse sequence. Responsive magnetic resonance signals detected by the RF coil 128, or a separate local coil, are received by the RF system 120, where they are amplified, demodulated, filtered, and digitized under direction of commands produced by the pulse sequence server 110. The RF system 120 includes an RF transmitter for producing a wide variety of RF pulses used in MRI pulse sequences. The RF transmitter is responsive to the scan prescription and direction from the pulse sequence server 110 to produce RF pulses of the desired frequency, phase, and pulse amplitude waveform. The generated RF pulses may be applied to the whole-body RF coil 128 or to one or more local coils or coil arrays.

The RF system 120 also includes one or more RF receiver channels. Each RF receiver channel includes an RF preamplifier that amplifies the magnetic resonance signal received by the coil 128 to which it is connected, and a detector that detects and digitizes the I and Q quadrature components of the received magnetic resonance signal. The magnitude of the received magnetic resonance signal may, therefore, be determined at any sampled point by the square root of the sum of the squares of the I and Q components:

$$M = \sqrt{I^2 + Q^2}\,;\qquad\qquad \text{Eqn. 1}$$

and the phase of the received magnetic resonance signal may also be determined according to the following relationship:

$$\varphi = \tan^{-1}\!\left(\frac{Q}{I}\right).\qquad\qquad \text{Eqn. 2}$$

The pulse sequence server 110 also optionally receives patient data from a physiological acquisition controller 130. By way of example, the physiological acquisition controller 130 may receive signals from a number of different sensors connected to the patient, such as electrocardiograph ("ECG") signals from electrodes, or respiratory signals from a respiratory bellows or other respiratory monitoring device. Such signals are typically used by the pulse sequence server 110 to synchronize, or "gate," the performance of the scan with the subject's heart beat or respiration.

The pulse sequence server 110 also connects to a scan room interface circuit 132 that receives signals from various sensors associated with the condition of the patient and the magnet system. It is also through the scan room interface circuit 132 that a patient positioning system 134 receives commands to move the patient to desired positions during the scan.

The digitized magnetic resonance signal samples produced by the RF system 120 are received by the data acquisition server 112. The data acquisition server 112 operates in response to instructions downloaded from the operator workstation 102 to receive the real-time magnetic resonance data and provide buffer storage, such that no data is lost by data overrun. In some scans, the data acquisition server 112 does little more than pass the acquired magnetic resonance data to the data processor server 114. However, in scans that require information derived from acquired magnetic resonance data to control the further performance of the scan, the data acquisition server 112 is programmed to produce such information and convey it to the pulse sequence server 110. For example, during prescans, magnetic resonance data is acquired and used to calibrate the pulse sequence performed by the pulse sequence server 110. As another example, navigator signals may be acquired and used to adjust the operating parameters of the RF system 120 or the gradient system 118, or to control the view order in which k-space is sampled. In still another example, the data acquisition server 112 may also be employed to process magnetic resonance signals used to detect the arrival of a contrast agent in a magnetic resonance angiography ("MRA") scan. By way of example, the data acquisition server 112 acquires magnetic resonance data and processes it in real-time to produce information that is used to control the scan.

The data processing server 114 receives magnetic resonance data from the data acquisition server 112 and processes it in accordance with instructions downloaded from the operator workstation 102. Such processing may, for example, include one or more of the following: reconstructing two-dimensional or three-dimensional images by performing a Fourier transformation of raw k-space data; performing other image reconstruction techniques, such as iterative or backprojection reconstruction techniques; applying filters to raw k-space data or to reconstructed images; generating functional magnetic resonance images; calculating motion or flow images; and so on.

Images reconstructed by the data processing server 114 are conveyed back to the operator workstation 102. Images may be output to operator display 112 or a display 136 that is located near the magnet assembly 124 for use by attending clinician. Batch mode images or selected real time images are stored in a host database on disc storage 138. When such images have been reconstructed and transferred to storage, the data processing server 114 notifies the data store server 116 on the operator workstation 102. The operator workstation 102 may be used by an operator to archive the images, produce films, or send the images via a network to other facilities.

The MRI system 100 may also include one or more networked workstations 142. By way of example, a networked workstation 142 may include a display 144, one or more input devices 146 (such as a keyboard and mouse or the like), and a processor 148. The networked workstation 142 may be located within the same facility as the operator workstation 102, or in a different facility, such as a different healthcare institution or clinic. The networked workstation 142 may include a mobile device, including phones or tablets.

The networked workstation 142, whether within the same facility or in a different facility as the operator workstation 102, may gain remote access to the data processing server 114 or data store server 116 via the communication system 140. Accordingly, multiple networked workstations 142 may have access to the data processing server 114 and the data store server 116. In this manner, magnetic resonance data, reconstructed images, or other data may exchange between the data processing server 114 or the data store server 116 and the networked workstations 142, such that the data or images may be remotely processed by a networked workstation 142. This data may be exchanged in any suitable format, such as in accordance with the transmission control protocol ("TCP"), the internet protocol ("IP"), or other known or suitable protocols.

The present disclosure describes a system and method for $T_1$ relaxation enhanced steady state ($T_1$RESS) MR imaging that suppresses fluid signal and modifies tissue contrast. In particular, tissue contrast in a steady-state acquisition is altered by periodically applying a contrast-modifying (CM) low flip angle RF pulse during the steady-state acquisition. The $T_1$RESS technique enables the efficient acquisition of steady-state MRI with a flexible degree of $T_1$ weighting. In an embodiment, the disclosed system and method may be used to enable high-quality non-contrast ungated MR angiography by suppressing fluid signal that might otherwise obscure the signal from arterial blood. In another embodiment, the system and method may also be used to suppress fluid signal on cine images of the heart, which might otherwise mimic the appearance of flowing blood. In yet another embodiment, the system and method may be used for contrast-enhanced MRI. The repeated application of a CM RF pulse introduces additional $T_1$ weighting and, therefore, makes the steady-state sequence sensitive to the effects of a paramagnetic contrast agent. For contrast-enhanced MRI, the $T_1$RESS technique provides marked improvement in image quality, contrast-to-noise ratio, and vascular conspicuity compared with conventional imaging techniques. For non-contrast magnetic resonance angiography (NCMRA), the $T_1$RESS technique depicts vascular anatomy and pathology with excellent image quality and spatial resolution comparable to CT angiography, using a workflow that obviates the need for scout imaging, contrast agents, breath-holding, or cardiac synchronization.

Figure 2:
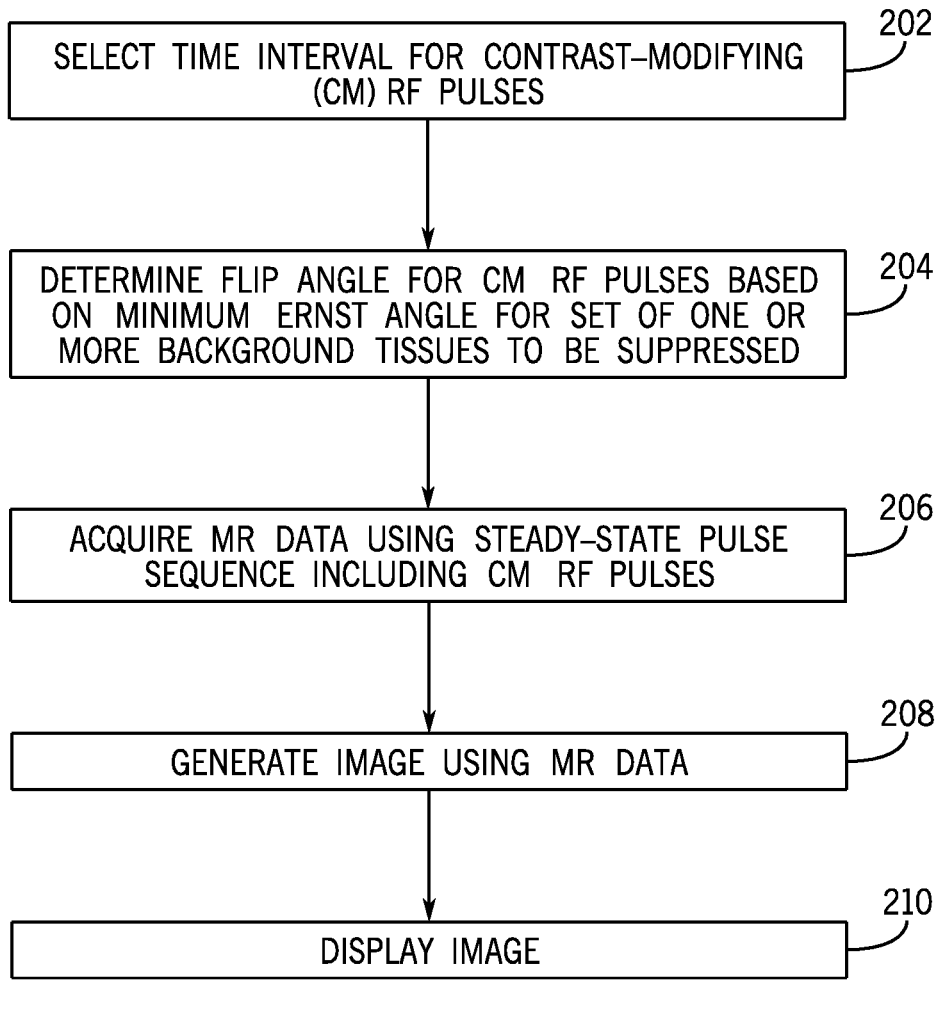
FIG. 2 illustrates a method for creating a magnetic resonance (MR) image of a subject in accordance with an embodiment.

FIG. 2 illustrates a method for creating a magnetic resonance (MR) image of a subject in accordance with an embodiment. As mentioned above, the system and method described herein for $T_1$ relaxation enhanced steady-state imaging combines a steady-state pulse sequence with periodically applied contrast-modifying (CM) partial saturation RF pulses to modify tissue contrast and suppress fluid signal. At block 202, a time interval, $\tau$, is selected for periodic application of a CM RF pulse during a steady-state acquisition. The time interval, $\tau$, is the time interval between application of successive CM RF pulses. The time interval, $\tau$, may be selected to provide an efficient imaging sequence and sufficient $T_1$ contrast. In an embodiment, the CM RF pulses are applied infrequently, for example, at intervals greater than 50 ms (i.e., $\tau$>50 ms), so that scan efficiency is maintained, and scan time is only marginally increased. In another embodiment, the CM RF pulses may be applied at regular intervals on the order of 100 to 400 ms throughout the duration of the steady-state acquisition.

At block 204, the flip angle ($\alpha_{CM}$) for the CM RF pulses that are applied at the periodic intervals, $\tau$, is determined based on a minimum Ernst angle for a set of one or more background tissues in the region of interest that the CM RF pulse is used to suppress with respect to a tissue of interest. In one embodiment, the CM RF pulses have a flip angle, $\alpha_{CM}$, that is greater than half the minimum Ernst angle of the set of one or more background tissues as given by:

$$\alpha_{CM} > 0.5 \times \cos^{-1}\left(e^{-\tau/T_{1min}}\right) \qquad \text{Eqn. 3}$$

where $\alpha_{CM}$ is the flip angle in degrees of the CM RF pulse, $\cos^{-1}$ is the inverse cosine function yielding degrees (not radians), e is the mathematical constant approximately equal to 2.71828, 1 is the time interval between application of successive CM RF pulses, and $T_{1\ min}$ is the shortest longitudinal relaxation time in the set of one or more background tissues the CM RF pulse should suppress. In this embodiment, the factor, 0.5, was chosen to be low for additional suppression by the imaging readout, and to account for other factors such as, for example, inflow which may artificially enhance the appearance of inflowing blood, while still providing adequate blood-to-background contrast. The same flip angle may be used for each CM RF pulse throughout the steady-state acquisition or one or more CM RF pulses applied during an acquisition may have a different flip angle. In one embodiment, the background tissue to be suppressed is fluid and the tissue of interest is blood. In another embodiment, the background tissue to be suppressed is unenhanced myocardium and the tissue of interest is enhanced myocardium. In yet another embodiment, the background tissue to be suppressed is normal tissue and the tissue of interest is abnormally enhancing tissue such as a tumor or inflammation.

At block 206, MR data is acquired by performing a steady-state pulse sequence including periodically applied CM RF pulses (a $T_1$ relaxation enhanced steady-state sequence) using, for example, an MRI system (e.g., MRI system 100 shown in FIG. 1). As described above, CM RF pulses are applied at the selected time interval, $\tau$, with the selected flip angle, $\alpha_{CM}$. In an embodiment, the CM RF pulses may be slice selective. The steady-state pulse sequence may be, for example, an un-balanced steady-state free precession (SSFP) pulse sequence, a balanced steady-state free precession (bSSFP) sequence, a fast interrupted steady-state (FISS) sequence, or other steady-state pulse sequence type such as a fast imaging with steady-state precession (FISP) sequence, a spoiled gradient echo sequence or a fast low angle shot (FLASH) sequence. The steady-state pulse sequence may be configured for a two-dimensional (2D) or three-dimensional (3D) acquisition. In order to avoid disruption of the steady-state magnetization when each CM RF pulse is applied during the steady-state acquisition, in an embodiment the CM RF pulse may be preceded by an $\alpha/2$ store RF pulse (where a is the imaging flip angle) to flip the magnetization along the longitudinal axis, followed by another $\alpha/2$ restore RF pulse of opposite polarity to flip the magnetization back into the transverse plane.

At block 208, an image (e.g., an angiogram) may be generated using the acquired MR data from block 206. As mentioned above, the generated image will have fluid signal suppression and $T_1$ contrast. The image may be generated using known reconstruction methods. At block 210, the image may be displayed to a user on a display (e.g., display 104, 136 or 144 shown in FIG. 1). The image may also be stored in in memory or data storage of, for example, an MRI system (e.g., the MRI system 100 of FIG. 1) or other computer system.

Figure 3:
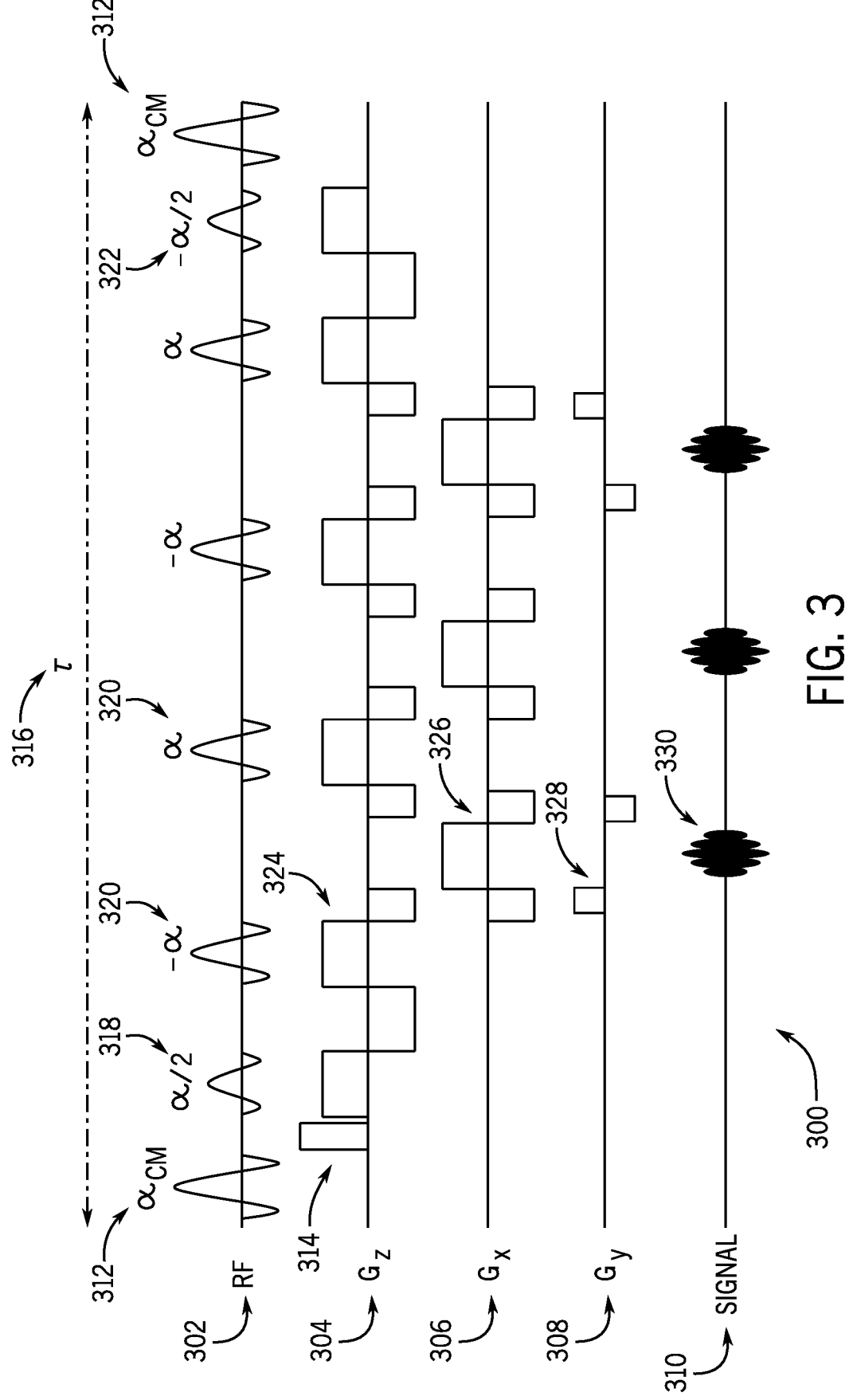
FIG. 3 is a pictorial representation of a $T_1$ relaxation enhanced steady-state ($T_1$RESS) pulse sequence in accordance with an embodiment.

As mentioned, various steady-state pulse sequences may be combined with the periodically applied CM RF pulses to provide a $T_1$ relaxation enhanced steady-state technique. FIG. 3 is a pictorial representation of a $T_1$ relaxation enhanced steady-state ($T_1$RESS) pulse sequence in accordance with an embodiment. In FIG. 3, the steady-state pulse sequence is a balanced steady-state free precession (bSSFP) sequence. The $T_1$ relaxation enhanced steady-state sequence 300 provides the capability to flexibly modulate the amount of $T_1$ weighting in an MR image while maintaining high scan efficiency. In FIG. 3, axis 302 is the axis for radio frequency (RF) pulses, axis 304 is the slice-selection direction, axis 306 is the frequency encoding direction, axis 308 is the phase encoding direction, and axis 310 is the generated signal. The sequence 300 uses an interrupted balanced steady-state free precession readout. In accordance with an embodiment, to suppress signal from one or more background tissues in a region of interest, for example, fluid, and to modify tissue contrast, a CM RF pulse 312 with a flip angle $\alpha_{CM}$ is applied followed by gradient spoiling using a gradient 314 in the slice-selection direction 304. As discussed above, the time interval, $\tau$ 316 (the time interval between application of successive CM RF pulses 312), is selected for periodic application of a CM RF pulse 312 during a steady-state acquisition and the flip angle $\alpha_{CM}$ for the CM RF pulse 312 is selected according to $$\alpha_{CM} > 0.5 \times \cos^{-1}\left(e^{-\tau/T_{1min}}\right),$$

where $\cos^{-1}$ is the inverse cosine function yielding degrees (not radians) and $T_{1\ min}$ is the shortest longitudinal relaxation time in the set of one or more background tissues the CM RF pulse is used to suppress. Accordingly, the flip angle $\alpha_{CM}$ for each CM RF pulse is determined based on a minimum Ernst angle for the set of one or more background tissues in the region of interest that the CM RF pulse 312 is used to suppress with respect to a tissue of interest.

In an embodiment, an $\alpha/2$ RF pulse 318 (where a is the imaging flip angle) is applied after the CM RF pulse 312 and gradient spoiler 314 to restore the magnetization in the longitudinal axis to the transverse plane prior to application of the $\pm\alpha$ imaging RF pulses 320. An $-\alpha/2$ pulse 322 is applied immediately prior to each application of the CM RF pulse 312 to store the magnetization in the transverse plane to the longitudinal axis. While the magnetization is stored along the longitudinal axis, the CM RF pulse 312 may be applied without disrupting the steady-state magnetization.

In FIG. 3, slice-selection gradients 324 are also applied in the slice direction 304 to excite a slice in the subject, frequency-encoding gradient 326 are applied in the frequency-encoding direction 306 and phase-encoding gradients 328 are applied on the phase-encoding direction 308. While one $\tau$ for the sequence 300 is shown, it should be understood that the sequence would repeat until all k-space data are sampled, with CM RF pulses 312 applied at the time interval, $\tau$, throughout the steady-state acquisition. While three imaging echo signals 330 following the $\pm\alpha$ imaging RF pulses 320 (i.e., n=3) are shown for the sequence 300 between the CM RF pulses, it should be understood that the number of +a pulses followed by echo signals may range from 1 to several hundred.

In some aspects, using a radial k-space trajectory offers improvements over a Cartesian k-space trajectory. For example, the need for a waiting period may be obviated by use of a radial k-space trajectory and optimized azimuthal view angles that suppress image artifacts. In some aspects, when multiple bSSFP readouts are collected (i.e. n>1), radial sampling is less sensitive than Cartesian sampling to artifacts caused by mild signal fluctuations arising from the interrupted nature of the contrast-modified pulse sequence, for example, the sequence in FIG. 3. With Cartesian k-space sampling, these signal fluctuations produce ghost artifacts in the phase-encoding direction. Conversely, these small signal variations produce minimal to no apparent artifacts with radial sampling. By distributing the signal fluctuations over a large (>540 degrees) azimuthal range of radial views, radial sampling is highly effective at minimizing image artifacts due to the signal fluctuations. In other aspects, due to oversampling of central k-space, radial sampling is less sensitive than Cartesian sampling to motion and arterial pulsation artifacts.

The pulse sequence described with respect to FIG. 3 can also be combined with other imaging techniques. In one non-limiting example, the described technique can be combined with cine imaging which may be used to portray multiple phases of the cardiac cycle. In another example, data acquisition performed using the described technique may be accelerated using accelerated imaging techniques, such as radial under sampling, compressed sensing, or simultaneous multi-slice acquisitions. In another example, the described technique may be combined with motion reduction techniques such as navigator gating or motion correction. In another example, two or more echoes may be acquired to permit the use of a Dixon reconstruction technique to create water-only and fat-only images.

In an embodiment, magnetic resonance (MR) images of a subject may be generated by performing a steady-state pulse sequence to acquire MR data from a region of interest in the subject. The steady-state pulse sequence may be performed using an MRI system. The steady-state pulse sequence includes a contrast-modifying (CM) radio frequency (RF) pulse applied periodically at a predetermined time interval followed by a gradient spoiler pulse. In an embodiment, the predetermined time interval may be greater than 50 ms. The CM RF pulse has a flip angle with a value determined based on a minimum Ernst angle for a set of one or more background tissues in the region of interest that the CM RF pulse is configured to suppress with respect to a tissue of interest. An image with $T_1$ contrast may be generated based on the acquired MR data. In an embodiment, the generated image may be displayed on a display. The set of one or more background tissues may include, for example, a fluid, an unenhanced myocardium, or a normal tissue and the tissue of interest may include, for example, blood, enhanced myocardium, or an abnormally enhancing tissue, respectfully. The abnormally enhancing tissue may be, for example, a tumor or inflammation.

In one embodiment, the flip angle of the CM RF pulse has a value greater than half the minimum Ernst angle for the set of one or more background tissues in the region of interest that the CM RF pulse is configured to suppress with respect to the tissue of interest and is determined using Eqn. 3 above, namely, $$\alpha_{CM} > 0.5 \times \cos^{-1}\left(e^{-\tau/T_{1min}}\right),$$

where $\alpha_{CM}$ is the flip angle in degrees of the CM RF pulse, $\cos^{-1}$ is the inverse cosine function yielding degrees (not radians), e is the mathematical constant approximately equal to 2.71828, t is the predetermined time interval, and $T_{1\ min}$ is the shortest longitudinal relaxation time in the set of one or more background tissues the CM RF pulse is configured to suppress. In an embodiment, the steady-state pulse sequence also includes a $\alpha/2$ store RF pulse applied prior to the CM RF pulse and an $\alpha/2$ restore RF pulse applied following to the CM RF pulse. The CM RF pulse may be slice selective. In various embodiments, the steady-state pulse sequence may be, for example, a steady-state free precession (SSFP) pulse sequence, a balanced steady-state free precession (bSSFP) pulse sequence, a fast interrupted steady-state (FISS) pulse sequence, a gradient echo based pulse sequence, or a fast imaging with steady-state precession (FISP) pulse sequence. The balanced steady-state free precession pulse sequence may be used, for example, for a cine acquisition or an MR angiography acquisition. In another embodiment, the steady-state pulse sequence may be accelerated using radial undersampling, compressed sensing, or simultaneous multi-slice. In yet another embodiment, performing the steady-state pulse sequence may include performing a motion reduction technique. In various other embodiments, the steady-state pulse sequence may be performed before, during, or after the administration (e.g., injection) of a contrast agent (e.g., a paramagnetic contrast agent such as gadolinium).

Computer-executable instructions for generating magnetic resonance (MR) images according to the above-described methods may be stored on a form of computer readable media. Computer readable media includes volatile and nonvolatile, removable, and non-removable media implemented in any method or technology for storage of information such as computer readable instructions, data structures, program modules or other data. Computer readable media includes, but is not limited to, random access memory (RAM), read-only memory (ROM), electrically erasable programmable ROM (EEPROM), flash memory or other memory technology, compact disk ROM (CD-ROM), digital volatile disks (DVD) or other optical storage, magnetic cassettes, magnetic tape, magnetic disk storage or other magnetic storage devices, or any other medium which can be used to store the desired instructions and which may be accessed by a system (e.g., a computer), including by internet or other computer network form of access.

The present invention has been described in terms of one or more preferred embodiments, and it should be appreciated that many equivalents, alternatives, variations, and modifications, aside from those expressly stated, are possible and within the scope of the invention.

We claim:

1. A method for generating magnetic resonance (MR) images of a subject, the method comprising:

performing, using a magnetic resonance imaging (MRI) system, a steady-state pulse sequence to acquire MR data from a region of interest in the subject, the steady-state pulse sequence comprising a contrast-modifying (CM) radio frequency (RF) pulse for $T_1$-weighting applied periodically at a predetermined time interval throughout an acquisition of a plurality of echo signals using a plurality of imaging RF pulses, the CM RF pulse applied at each predetermined time interval prior to acquisition of at least two of the plurality of echo signals, and the CM RF pulse having a flip angle with a value determined based on a minimum Ernst angle for a set of one or more background tissues in the region of interest that the CM RF pulse is configured to suppress with respect to a tissue of interest; and generating an image with $T_1$ contrast based on the acquired MR data.

2. The method according to claim 1, further comprising displaying the generated image on a display.

3. The method according to claim 1, wherein the set of one or more background tissues includes a fluid and the tissue of interest is blood.

4. The method according to claim 1, wherein the set of one or more background tissues includes an unenhanced myocardium and the tissue of interest is enhanced myocardium.

5. The method according to claim 1, wherein the set of one or more background tissues includes normal tissue and the tissue of interest is an abnormally enhancing tissue.

6. The method according to claim 5, wherein the abnormally enhancing tissue is one of a tumor or inflammation.

7. The method according to claim 1, wherein the flip angle of the CM RF pulse has a value greater than half the minimum Ernst angle for the set of one or more background tissues in the region of interest that the CM RF pulse is configured to suppress with respect to the tissue of interest and is determined using:

$$\alpha_{CM} > 0.5 \times \cos^{-1}\left(e^{-\tau/T_{1min}}\right)$$

where $\alpha_{CM}$ is the flip angle in degrees of the CM RF pulse, $\cos^{-1}$ is the inverse cosine function yielding degrees, e is the mathematical constant approximately equal to 2.71828, t is the predetermined time interval, and $T_{1\ min}$ is the shortest longitudinal relaxation time in the set of one or more background tissues the CM RF pulse is configured to suppress.

8. The method according to claim 1, wherein the steady-state pulse sequence further comprises an $\alpha/2$ store RF pulse applied prior to the CM RF pulse and an $\alpha/2$ restore RF pulse applied following to the CM RF pulse.

9. The method according to claim 1, wherein the CM RF pulse is slice selective.

10. The method according to claim 1, wherein the predetermined time interval is greater than 50 ms.

11. A magnetic resonance imaging (MRI) system comprising:

a magnet system configured to generate a polarizing magnetic field about at least a portion of a subject;

a plurality of gradient coils configured to apply at least one gradient field to the polarizing magnetic field;

a radio frequency (RF) system configured to apply an excitation field to the subject and to receive MR data from the subject; and a computer system programmed to:

perform, using the MRI system, a steady-state pulse sequence to acquire MR data from a region of interest in the subject, the steady-state pulse sequence comprising a contrast-modifying (CM) radio frequency (RF) pulse for $T_1$-weighting applied periodically at a predetermined time interval throughout an acquisition of a plurality of echo signals using a plurality of imaging RF pulses, the CM RF pulse applied at each predetermine time interval prior to acquisition of at least two of the plurality of echo signals, and the CM RF pulse having a flip angle with a value determined based on a minimum Ernst angle for a set of one or more background tissues in the region of interest that the CM RF pulse is configured to suppress with respect to a tissue of interest; and generate an image with $T_1$ contrast based on the acquired MR data.

12. The system according to claim 11, further comprising a display and wherein the computer system is further programmed to display the generated image on the display.

13. The system according to claim 11, wherein the set of one or more background tissues includes a fluid and the tissue of interest is blood.

14. The system according to claim 11, wherein the set of one or more background tissues includes unenhanced myocardium and the tissue of interest is enhanced myocardium.

15. The system according to claim 11, wherein the set of one or more background tissues includes a normal tissue and the tissue of interest is abnormally enhancing tissue.

16. The system according to claim 15, the abnormally enhancing tissue is one of a tumor or inflammation.

17. The system according to claim 11, wherein the flip angle of the CM RF pulse has a value greater than half the minimum Ernst angle for the set of one or more background tissues in the region of interest that the CM RF pulse is configured to suppress with respect to the tissue of interest and is determined using:

$$\alpha_{CM} > 0.5 \times \cos^{-1}\left(e^{-\tau/T_{1min}}\right)$$

where $\alpha_{CM}$ is the flip angle in degrees of the CM RF pulse, $\cos^{-1}$ is the inverse cosine function yielding degrees, e is the mathematical constant approximately equal to 2.71828, t is the predetermined time interval, and $T_{1\ min}$ is the shortest longitudinal relaxation time in the set of one or more background tissues the CM RF pulse is configured to suppress.

18. The system according to claim 11, wherein the pulse sequence further comprises an $\alpha/2$ store RF pulse applied prior to the CM RF pulse and an $\alpha/2$ restore RF pulse applied following to the CM RF pulse.

19. The system according to claim 11, wherein the CM RF pulse is slice selective.

20. The system according to claim 11, wherein the predetermined time interval is greater than 50 ms.

\* \* \* \* \*